United States Patent
Lee et al.

(10) Patent No.: US 11,186,828 B2
(45) Date of Patent: *Nov. 30, 2021

(54) METHOD OF MAKING HUMAN CELLS EXPRESSING OCT4, SOX2, AND NANOG USING AN ECKLONIA CAVA EXTRACT

(71) Applicant: BBHC CO., LTD., Seoul (KR)

(72) Inventors: Sang Yeon Lee, Gyeonggi-do (KR); Won Ju Jung, Seoul (KR); Ho Bin Kim, Seoul (KR); Min Sun Oh, Seoul (KR); Kye Ho Lee, Seoul (KR)

(73) Assignee: BBHC CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,606

(22) PCT Filed: Jun. 25, 2014

(86) PCT No.: PCT/KR2014/005618
§ 371 (c)(1),
(2) Date: Dec. 9, 2016

(87) PCT Pub. No.: WO2015/190636
PCT Pub. Date: Dec. 17, 2015

(65) Prior Publication Data
US 2017/0114328 A1    Apr. 27, 2017

(30) Foreign Application Priority Data
Jun. 13, 2014    (KR) .......................... 10-2014-0072427

(51) Int. Cl.
C12N 5/00    (2006.01)
C12N 5/074    (2010.01)
A61K 35/28    (2015.01)

(52) U.S. Cl.
CPC ............ *C12N 5/0696* (2013.01); *A61K 35/28* (2013.01); *C12N 2501/999* (2013.01); *C12N 2506/1384* (2013.01)

(58) Field of Classification Search
CPC ............ C12N 5/0696; C12N 2501/999; C12N 2506/1384; A61K 35/28
USPC ......................................................... 435/455
See application file for complete search history.

(56) References Cited

FOREIGN PATENT DOCUMENTS

KR    1020100021266    2/2010
KR    1020120134360    12/2012

OTHER PUBLICATIONS

Sun (Feeder-Free Derivation of induced pluripotent stem cells from adult human adipose stem cells, PNAS, Sep. 15, 2009, vol. 106, No. 37, p. 15720-15725).*
Feng (Cell Stem Cell, Apr. 3, 2009, vol. 4, p. 301-312).*
Robinton (Nature, May 2013, vol. 481, No. 7381, p. 295-305).*
Takahashi (Cell, 2006, vol. 126:663-676).*
Yu (Science, 2007, vol. 318, p. 1917-1920).*
Aoi (Science, Aug. 1, 2008, vol. 321, No. 5889, p. 699-702, available online Feb. 14, 2008).*
Nakagawa (Nat Biotechnol, Jan. 2008, vol. 26: 101-106).*
Hussein (Curr. Opin. Genetics & Develop., 2012, vol. 22, p. 435-443).*
Original priority document (KR2014/005618 and WO 2015190636) translation, 2018.*
Ali, T. F. et al., "Phlorotannin-incorporated mesenchymal stem cells and their promising role in osteogenesis imperfecta", Journal of Medical Hypotheses and Ideas, 2012, vol. 6(2), pp. 85-89.
Cho, H.J. et al., "Induction of pluripotent stem cells from adult somatic cells by protein-based reprogramming without genetic manipulation", Blood, 2010, vol. 116(3), pp. 386-395.
Kim, D. et al., "Generation of human induced pluripotent stem cells by direct delivery of reprogramming proteins", Cell Stem Cell, 2009, vol. 4(6), pp. 472-476.

* cited by examiner

*Primary Examiner* — Michael C Wilson
(74) *Attorney, Agent, or Firm* — Sughrue Mion, PLLC

(57) ABSTRACT

The present disclosure relates to a medium composition for r25/eprogramming induced pluripotent stem cells, containing an Ecklonia cava extract. Also, the present disclosure relates to a method for manufacturing induced pluripotent stem cells by using the medium composition. When the medium composition according to the present disclosure is used, induced pluripotent stem cells can be efficiently produced using adipose-derived mesenchymal stem cells safely and easily. The manufactured pluripotent stem cells are differentiable into various cells, and thus can be favorably used as a cell therapeutic agent.

3 Claims, 3 Drawing Sheets

[Fig. 1]
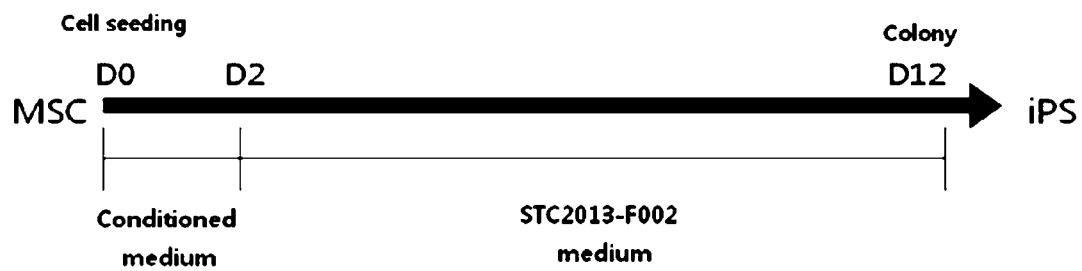
[Fig. 2]
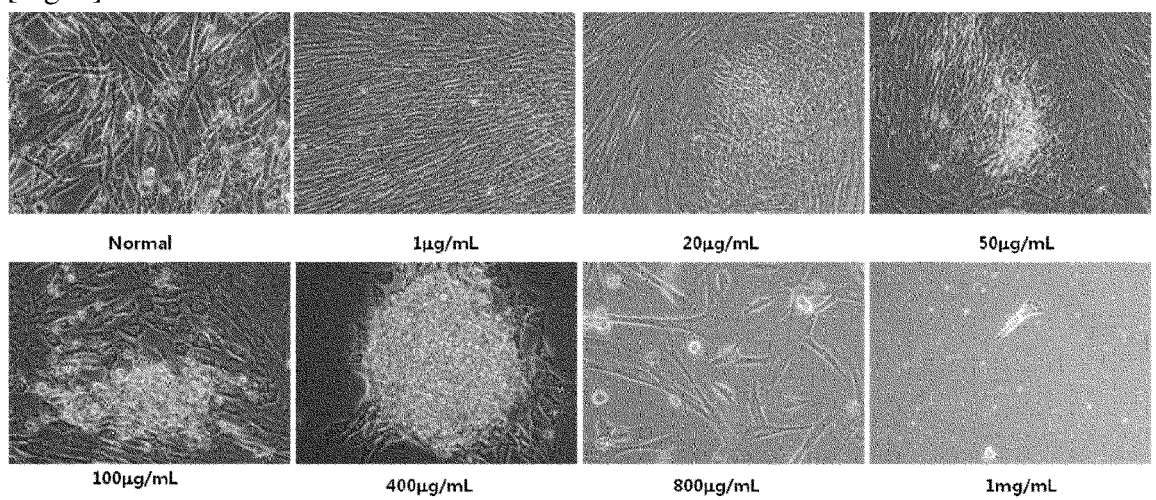
[Fig. 3]
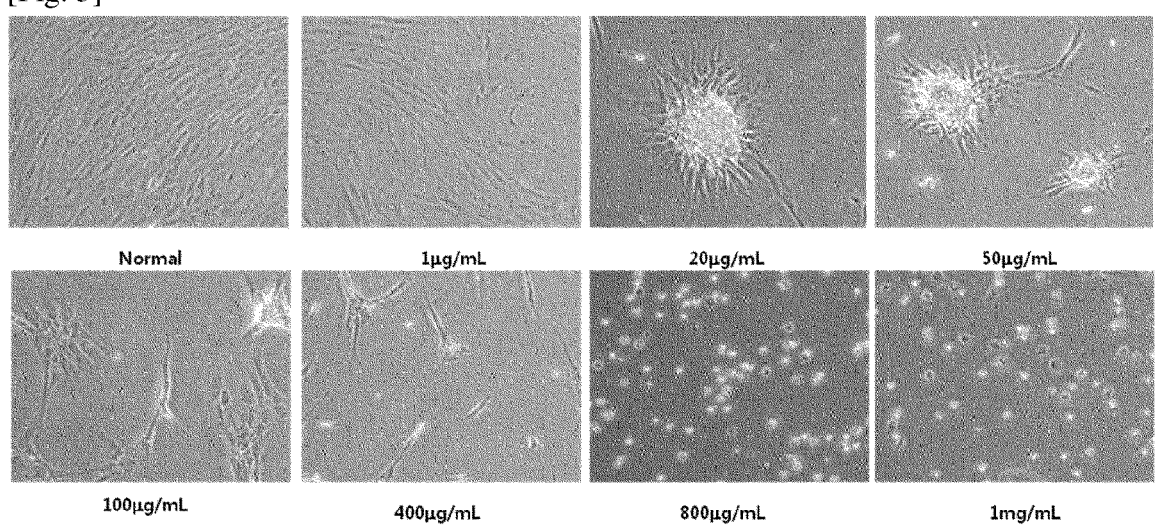

[Fig. 4]
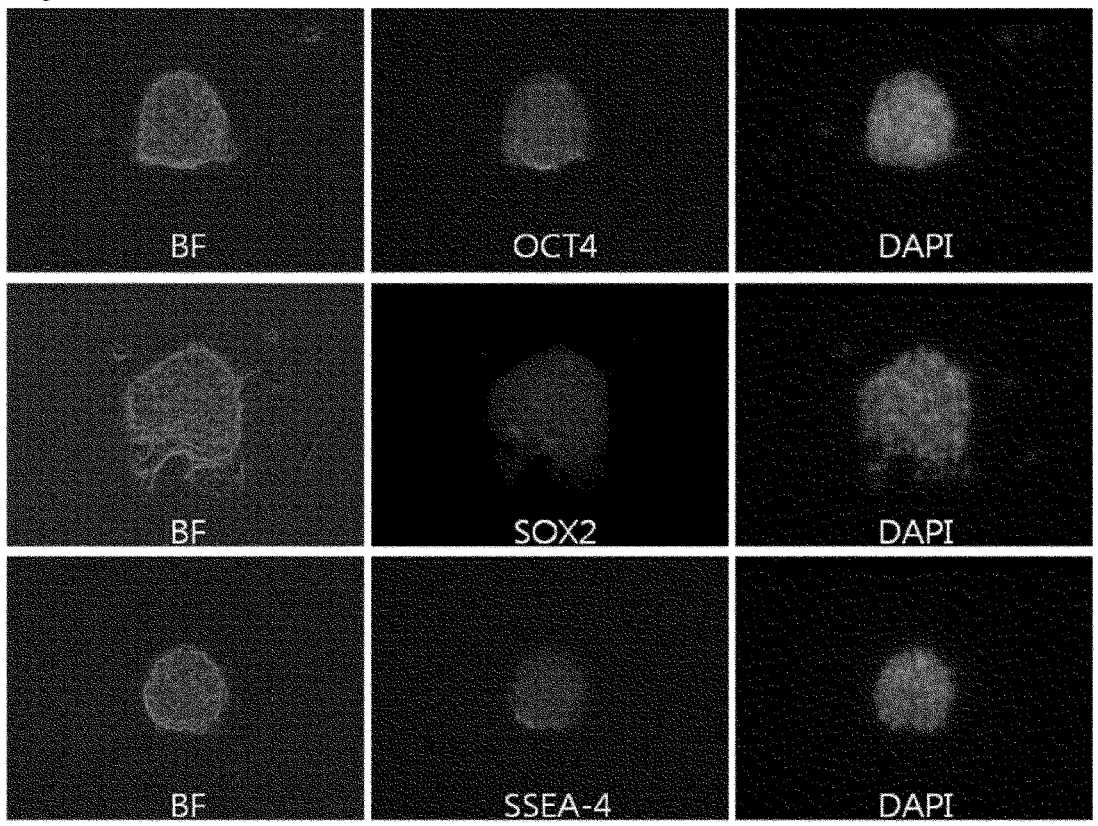
[Fig. 5]
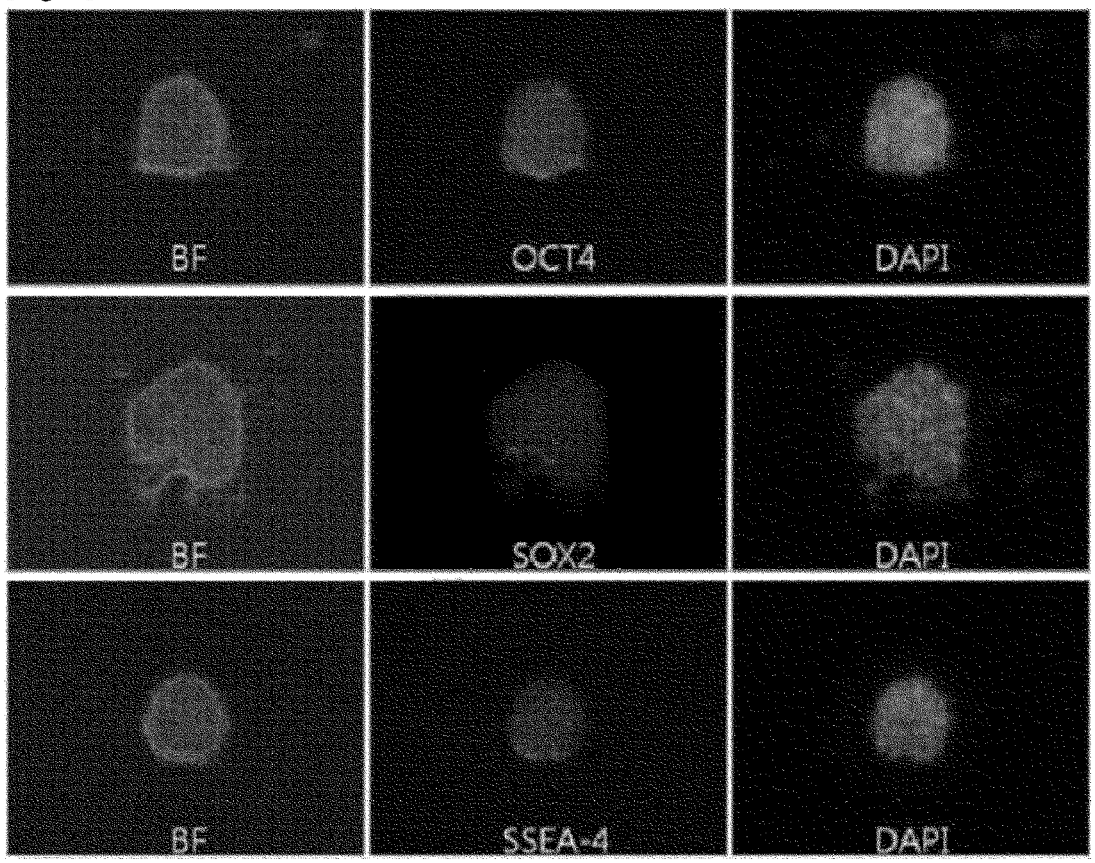

[Fig. 6]
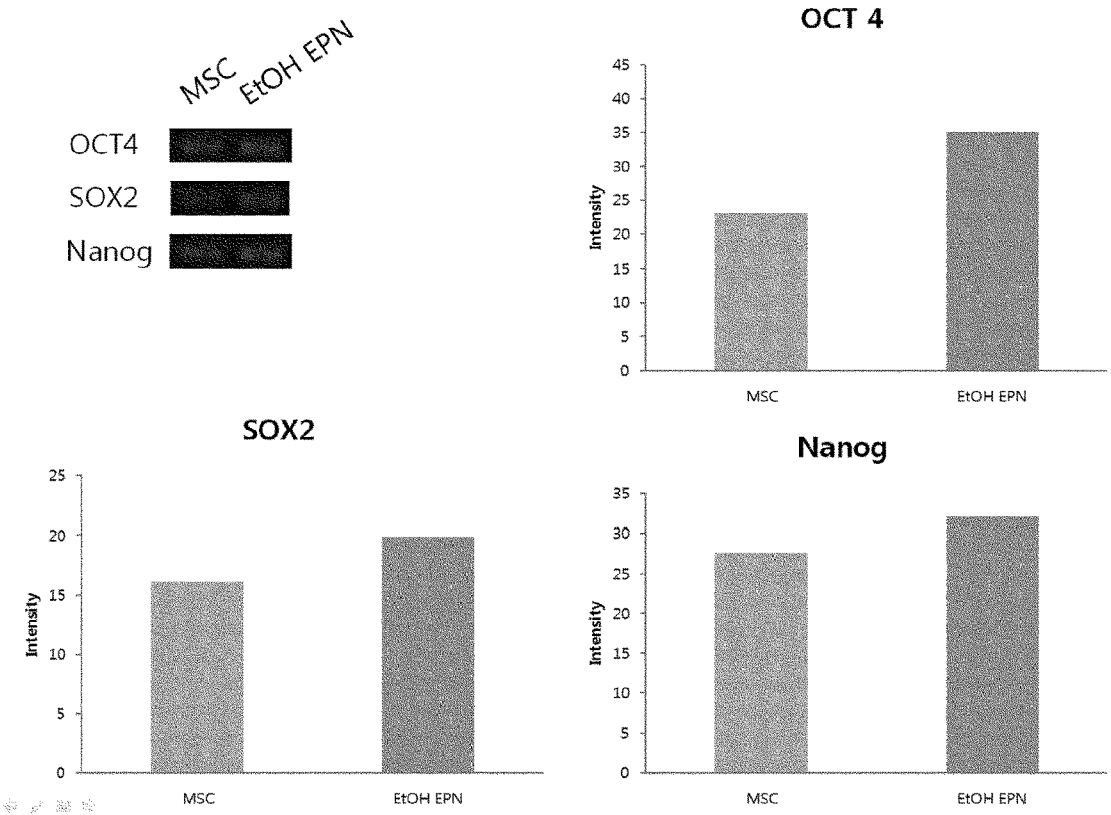
[Fig. 7]
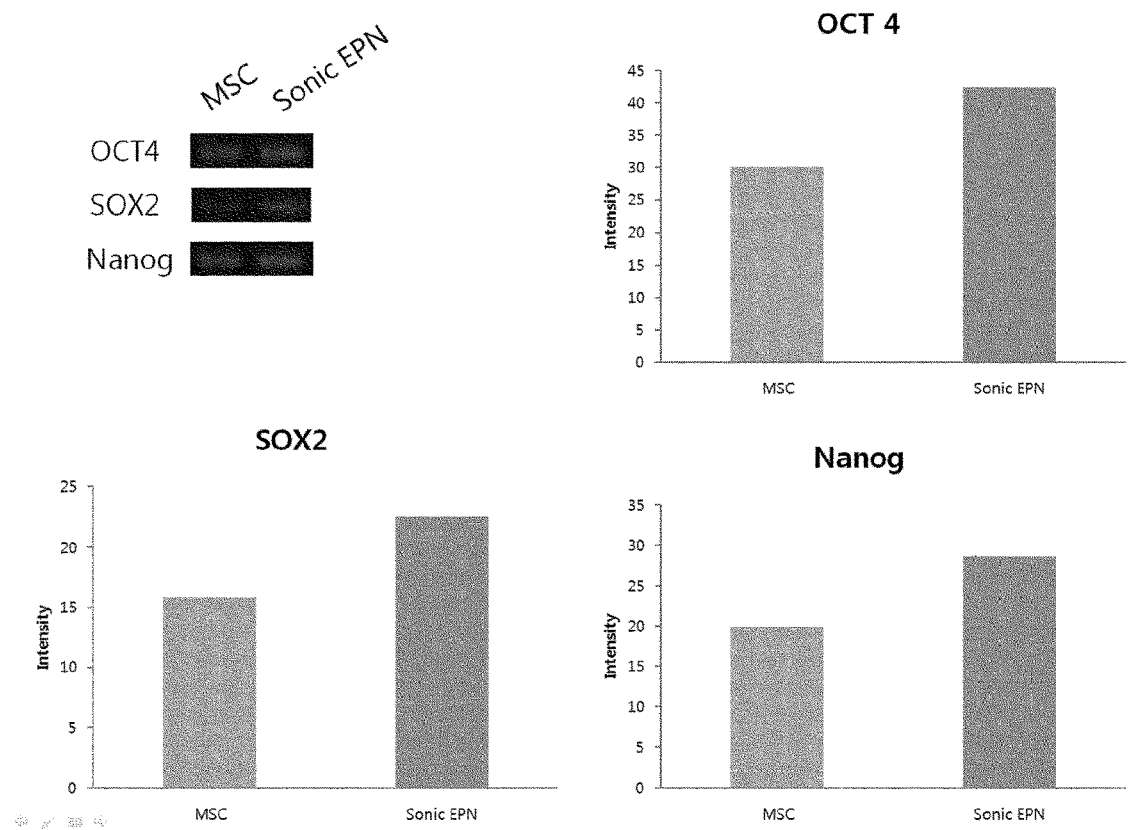

METHOD OF MAKING HUMAN CELLS EXPRESSING OCT4, SOX2, AND NANOG USING AN ECKLONIA CAVA EXTRACT

This application is a national stage application of International Patent Application No. PCT/KR2014/005618, filed Jun. 25, 2014, which claims priority to Korean Patent Application No. 10-2014-0072427, filed Jun. 13, 2014. The entirety of the aforementioned applications is incorporated herein by reference.

FIELD

The present disclosure relates to a pluripotent stem cell-induced medium composition of human adipose-derived mesenchymal stem cells and a method for manufacturing patient-customized induced pluripotent stem cells using the same.

BACKGROUND

Stem cells are collectively referred to as undifferentiated cells before differentiation that can be obtained from each tissue. The stem cells have a property capable of continuously making the same cells for a predetermined period in an undifferentiated state and a property capable of being into various cells configuring a biological tissue under a proper condition.

The stem cells may be largely classified into embryonic stem cells and adult stem cells depending on potency and a creation time. As another classification, the stem cells may be divided into pluripotent, multipotent, and unipotent stem cells depending on potency of the stem cells.

The adult stem cells may be classified into multipotent or unipotent stem cells. Representative adult stem cells include mesenchymal stem cells (MSCs) and hematopoietic stem cells (HSCs). The MSCs are differentiated into chondrocyte, osteoblast, adipocyte, myocyte, and neuron, and the HSCs are differentiated into blood cells in the blood including red blood cells, white blood cells, platelets, and the like.

On the other hand, the pluripotent stem cells are called stem cells having multifunctions which may be differentiated into three germ layers configuring a living body to be differentiated into all cells or organ tissues of the human body and generally, the embryonic stem cells correspond to the pluripotent stem cells. It is known that the human embryonic stem cells are made from the embryos which may be generated into the human organism to have many ethical issues, but have excellent cell proliferation and potency as compared with the adult stem cells. The adult stem cells may be obtained from bone marrow, blood, brain, skin, etc. to have less ethical issues, but have limited potency as compared with the embryonic stem cells.

As an alternative to overcome the problems, various methods for manufacturing customized pluripotent stem cells similar to the embryonic stem cells by reprogramming cells derived from the adult have been attempted. As a representative method, there are a fusion with ES cell method, a somatic cell nuclear transfer method, a reprogramming by gene factor method, and the like. The fusion with ES cell method has a problem in terms of cell stability because the induced cells have additional two pairs of genes, and the somatic cell nuclear transfer method has a problem in that a lot of ova are required and efficiency is too low. In addition, the reprogramming by gene factor method is a method using virus containing oncogenes in order to induce reprogramming by inserting a specific gene and has a problem in terms of development possibility of cell therapeutic agents due to a high risk of cancer occurrence, low efficiency, and difficulty in a methodical aspect.

In order to successfully obtain a large amount of pluripotent stem cells, a culture composition is very important in the step of culturing isolated adipose-derived monocytes, and thus researches for manufacturing a larger amount of pluripotent stem cells by an induction method with high efficiency are required.

Meanwhile, in some cases, Ecklonia cava is used for a composition for treating or preventing an atopic disease (Korean Patent Application Publication No. 2009-0043115) or a hairdye composition for oxidation dyeing (Korean Patent Application Publication No. 2012-0126148), but has been never used for reprogramming adipose-derived mesenchymal stem cells into induced pluripotent stem cells.

Details described in the above background are only for enhancement of understanding of the background of the present disclosure and therefore it may contain information that does not form the prior art that is already known in this country to a person of ordinary skill in the art.

SUMMARY

The inventors made an effort to find a method for inducing pluripotent stem cells with high efficiency for application of developing cell therapeutic agents having safety and high production efficiency. As a result, the inventors verified that when an Ecklonia cava extract as a safe natural extract was added in a cell culture medium, induced pluripotent stem cells may be manufactured with safety and high efficiency by using adipose-derived mesenchymal stem cells.

Therefore, the present disclosure has been made in an effort to provide a medium composition for reprogramming adipose-derived mesenchymal stem cells into induced pluripotent stem cells, containing an Ecklonia cava extract.

Further, the present disclosure has been also made in an effort to provide a method for manufacturing induced pluripotent stem cells including a step of reprogramming adipose-derived mesenchymal stem cells into induced pluripotent stem cells in a medium containing an Ecklonia cava extract.

Further, the present disclosure has been also made in an effort to provide induced pluripotent stem cells manufactured by the manufacturing method.

Further, the present disclosure has been also made in an effort to provide a patient-customized cell therapeutic composition including induced pluripotent stem cells manufactured by the manufacturing method by isolating stem cells from adipose of a patient.

Other objects and advantages of the present disclosure will be more apparent by the detailed description of the disclosure, claims, and drawings below.

An exemplary embodiment of the present disclosure provides a medium composition for reprogramming adipose-derived mesenchymal stem cells into induced pluripotent stem cells, containing an Ecklonia cava extract.

The inventors made an effort to find a method for inducing pluripotent stem cells with high efficiency for application of developing cell therapeutic agents having no ethical issues to destroy the embryo, no risk of forming cancer cells without using virus, and high safety and production efficiency. As a result, it is verified that when the Ecklonia cava extract as a safe natural extract is added in the cell culture medium, the induced pluripotent stem cells can be manufactured with significantly high efficiency.

Ecklonia cava which is an active ingredient included in the medium composition of the present disclosure is a perennial alga of a laminariaceous laminariales phaeophyta that mainly lives in the southern coast, the coast of the Jeju island, and the coast of the Ulleungdo island, mainly becomes food for abalone, turban, and the like, and used as a main raw material to make alginic acid or potassium iodide or for food.

The Ecklonia cava extract included in the present disclosure may be extracted by using water and organic solvents including (a) anhydrous or water-containing low alcohol having 1 to 4 carbons (methanol, ethanol, propanol, butanol, n-propanol, iso-propanol, n-butanol, etc.), (b) a mixed solvent of the low alcohol and water, (c) acetone, (d) ethyl acetate, (e) chloroform, (f) 1,3-butylene glycol, (g) hexane, (h) diethyl ether, and the like, and preferably, may be extracted by using a mixed solvent of methanol or ethanol and water, or using them respectively. In the case of extracting the Ecklonia cava extract by using the mixed solvent, the content of methanol or ethanol may be preferably 50 to 80 v/v %.

Currently, cases for applying the Ecklonia cava extract to skin compositions such as cosmetics have been increased (see Korean Patent Application Publication Nos. 2013-0017159, 2012-0040488, and 2010-0097293, etc.), but there is no case for developing the Ecklonia cava extract to pluripotent stem cell-induced media.

The term "embryonic stem cells" used in the present disclosure are called cells having pluripotency as cells which are isolated and cultured from an inner cell mass of blastocyst in the early days of its development after fertilization. The term "pluripotent stem cells" used in the present disclosure are called stem cells having pluripotency which may be differentiated into three germ layers configuring the living body, that is, an endoderm, a mesoderm, and an ectoderm.

The term "differentiation" used in the present disclosure means that while the cells are divided, proliferated, and grown, structures or functions thereof are specialized, that is, forms or functions are changed in order to perform tasks which are given to cells, tissues, and the like of an organism.

The term "cell therapeutic agent" of the present disclosure, as a drug used for treating, diagnosing, and preventing by using cells and tissues manufactured through isolation from the human, culture, and a specific manipulation, is referred to as a drug used for treating, diagnosing, and preventing through a series of actions such as proliferating and screening homogenous or heterogeneous cells for restoring functions of cells or tissues, changing a biological characteristic of the cells by another method, and the like. The cell therapeutic agents are largely classified into somatic cell therapeutic agents and stem cell therapeutic agents according to the degree of differentiation of cells, and the present disclosure relates to stem cell therapeutic agents.

The "mesenchymal stem cells" of the present disclosure are cells isolated from embryonic stem cells or adult stem cells derived from mammals, preferably adipose-derived mesenchymal stem cells, and more preferably human adipose-derived mesenchymal stem cells. The adipose-derived stem cells may be extracted and obtained from the adipose tissue of the human body. The extraction of the mesenchymal stem cells from the adipose may be performed by using various methods, and for example, in order to isolate monocytes from the adipose tissue, the adipose tissue is extracted from the human body and washed with a dulbecco's phosphate-buffered saline (DPBS) until the blood does not flow, and the washed adipose tissue is chopped with a surgical blade and incubated at 37° C. to obtain a solution containing monocytes.

The term "medium" used in the present disclosure means a mixture for culturing or differentiating cells such as stem cells in vitro, which contains essential elements for growth and proliferation of the cell including sugars, amino acids, various nutrients, serum, growth factors, minerals, and the like.

Particularly, the medium of the present disclosure is a medium for culturing the mesenchymal stem cells. In this case, the mesenchymal stem cells are cells isolated from embryonic stem cells or adult stem cells derived from mammals and cells having unlimitedly proliferating ability and differentiation to various cell forms (for example, adipocytes, chondrocytes, myocytes, osteocytes, etc.). Further, in the present disclosure, multipotent mesenchymal stem cells having immune phenotypes representing a positive reaction for antibodies to CD44, CD73, and CD90 and a negative reaction for antibodies to CD34 and CD45 are used.

Various media are commercialized in the art and may be artificially manufactured and used. For example, as the commercialized medium, a Dulbecco's modified eagle's medium (DMEM), a minimal essential medium (MEM), a basal medium eagle (BME), RPMI 1640, F-10, F-12, DMEM F-12, a α-minimal essential medium (α-MEM), a Glasgow's minimal essential medium (G-MEM), an Iscove's modified Dulbecco's medium (IMPM), AmnioMax, an AmnioMax II complete medium (Gibco, Newyork, USA), and a Chang's medium MesemCult-XF medium (STEMCELL Technologies, Vancouver, Canada), and the like are included, and may be used as a basic medium included in the medium composition of the present disclosure in addition to a medium which may be artificially manufactured.

In the basic medium, generally added serum ingredients (for example, fetal bovine serum (FBS)), antibiotics (for example, penicillin and streptomycin), and the like may be added. The concentration of the serum ingredient or the antibiotic ingredient which is added in the basic medium may be modified within a range that can achieve the effect of the present disclosure, and preferably, 10% FBS, 100 unit/ml of penicillin, 50 μg/ml of streptomycin, and the like may be added.

Further, the medium of the present disclosure may additionally include a nutrient mixture. The nutrient mixture is a mixture containing various amino acids, vitamins, inorganic salts, and the like which are generally used in a cell culture and may use a nutrient mixture which is manufactured by mixing the amino acids, the vitamins, the inorganic salts, and the like or commercially manufactured. The commercially manufactured nutrient mixture may include M199, MCDB110, MCDB202, MCDB302, and the like as an example, but is not limited thereto.

Further, the medium of the present disclosure may additionally include energy water for induction and stabilization of the pluripotent stem cells. The energy water is preferably added with 0.01 to 10 v/v % and more preferably 0.05 to 0.5 v/v %.

The medium composition of the present disclosure is a pluripotent stem cell-induced specific medium and may be achieved by adding the Ecklonia cava extract to the basic medium, and may include the Ecklonia cava extract at a concentration of preferably 1 to 1,000 μg/ml and more preferably 10 to 400 μg/ml based on the entire medium composition.

According to another aspect of the present disclosure, the present disclosure provides a method for manufacturing induced pluripotent stem cells including: adding an Ecklonia cava extract in a cell culture medium; and reprogramming adipose-derived mesenchymal stem cells into induced pluripotent stem cells in the medium.

According to an exemplary embodiment of the present disclosure, in a case of using a medium composition including the Ecklonia cava extract of the present disclosure as an experimental group (a medium containing the Ecklonia cava extract and energy water in a DMEM F-12 medium), unlike a case of using only the DMEM F-12 medium as a control group, it is verified that at 8-th to 10-th days, colonies of pluripotent stem cells are formed (see FIGS. 2 and 3).

According to yet another aspect of the present disclosure, the present disclosure provides induced pluripotent stem cells manufactured by the manufacturing method.

The induced pluripotent stem cells of the present disclosure have the same potency as the embryonic stem cells and are almost the same as the embryonic stem cells even in shapes of the cells (see FIGS. 2 and 3). According to an exemplary embodiment of the present disclosure, as a result of examining whether to express specific genes Oct4 and Sox-2 and protein SSEA-4 in the embryonic stem cells, it is verified that the genes and proteins are expressed like the embryonic stem cells in the pluripotent stem cells induced by the present disclosure (see FIGS. 4 and 5).

According to another exemplary embodiment, in the mesenchymal stem cells (MSC) without induction, an expression level of specific genes OCT4, SOX2, and Nanog of the pluripotent stem cells is low, whereas in the pluripotent stem cells induced by the method of the present disclosure (Experimental Example 1-1: EtOH EPN, Experimental Example 1-2: Sonic EPN), these specific genes are significantly higher expressed (see FIGS. 6 and 7).

According to still another aspect of the present disclosure, the present disclosure provides a cell therapeutic composition containing the induced pluripotent stem cells manufactured by the manufacturing method.

The composition of the present disclosure may be administrated by any administration route, particularly, a method such as peritoneal or thoracic cavity administration, subcutaneous administration, intravenous or endovascular administration, intramuscular administration, local administration by injection, or the like.

In the present disclosure, the composition may be administrated in a form such as injections, suspensions, and emulsions on the basis of a general method, and if necessary, may be suspended in an adjuvant such as a Freund's complete adjuvant or administrated together with a material having an adjuvant activity such as BCG. The composition may be sterilized or contain adjuvants including stabilizers, wetting or emulsifying accelerators, salts or buffers for adjusting the osmotic pressure, and the like and other therapeutically available materials.

The cell therapeutic composition of the present disclosure can be applied to arthritis, neurological disorders, endocrine disorders, liver diseases, and the like and has a possibility to an allogenic therapeutic agent for the human according to clinical trial results for the human later.

Features and advantages of the present disclosure are as follows.

(i) The present disclosure provides a medium composition for reprogramming induced pluripotent stem cells containing an Ecklonia cava extract.

(ii) Further, the present disclosure provides a method for manufacturing induced pluripotent stem cells using the medium composition.

(iii) Induced pluripotent stem cells can be effectively manufactured by using adipose-derived mesenchymal stem cells by using the medium composition according to the present disclosure, and the manufactured pluripotent stem cells can be differentiated into various cells to be useful as a cell therapeutic agent.

(iv) In the present disclosure, the pluripotent stem cells having the same potency as the embryonic stem cells are manufactured and thus safe pluripotent stem cells having no ethical issues to destroy the embryo without using the embryonic stem cells and no risk of forming cancer cells without using virus which may cause the cancer can be manufactured.

(v) Further, the pluripotent stem cells can be manufactured very easily and with significantly high efficiency compared to the existing method by using a natural extract and it is expected to accelerate the application of patient-customized stem cell therapeutic agents by using the mesenchymal stem cells isolated from the adipocytes of the patient. The present disclosure is considered to largely contribute to the treatment of various intractable diseases such as Neurological diseases and immune diseases.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a diagram illustrating that substantially the same pluripotent stem cells as embryonic stem cells are induced in adipose-derived mesenchymal stem cells by injecting and culturing an Ecklonia cava extract medium.

FIG. 2 illustrates formation of colonies of pluripotent stem cells induced according to a concentration of an Ecklonia cava extract (an ethanol extract) by a method (Example 1-1) of the present disclosure.

FIG. 3 illustrates formation of colonies of pluripotent stem cells induced according to a concentration of an Ecklonia cava extract (a water extract) by a method (Example 1-2) of the present disclosure.

FIG. 4 verifies that pluripotent stem cells induced by a method (Experimental Example 1-1) of the present disclosure are pluripotent stem cells by using specific-protein expression.

FIG. 5 verifies that pluripotent stem cells induced by a method (Experimental Example 1-2) of the present disclosure are pluripotent stem cells by using specific-protein expression.

FIG. 6 illustrates gene expression of pluripotent stem cells induced by the method (Experimental Example 1-1) of the present disclosure by a graph.

FIG. 7 illustrates gene expression of pluripotent stem cells induced by the method (Experimental Example 1-2) of the present disclosure by a graph.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in more detail through Examples. However, the present disclosure is not limited to the exemplary embodiments disclosed below, but can be implemented in various forms. The following exemplary embodiments are described in order to enable those of ordinary skill in the art to embody and practice the disclosure.

EXAMPLES

Example 1: Preparation of Ecklonia cava Extract

1.) Example 1-1: Preparation of Ecklonia cava Extract Using Ethanol Solvent Herb medicine samples used in an experiment were purchased in the Jeju island, exactly evaluated by the expert, and used in the experiment. 100 g of a dried herb medicine sample was added in 1 L of 70% ethanol, reflux-extracted for 16 hours with ethanol, and filtrated by using a filter. A filtrate was concentrated in a rotary decompression evaporator and immediately lyophilized.

2.) Example 1-2: Preparation of Ecklonia cava Extract Using Water

Herb medicine samples used in an experiment were purchased in the Jeju island, exactly evaluated by the expert, and used in the experiment. 100 g of a dried herb medicine sample was added in 1 L of water, extracted for 16 hours with water by applying an ultrasonic extractor, and filtrated by using a filter. A filtrate was concentrated in a rotary decompression evaporator and immediately lyophilized.

Example 2: Isolation and Incubation of Mesenchymal Stem Cells from Human Adipose Tissue

1). Example 2-1: Extraction of Human Adipose Tissue

The adipose tissue was immediately collected after liposuction. Before the sample was transferred to a laboratory, the adipose tissue suctioned in a sterile glass bottle of 500 ml was collected. Thereafter, the sterile glass bottle was sealed and then transferred to the laboratory. In the laboratory, mesenchymal stem cells were extracted in a flow hood of class 100 under a sterile condition. The sample was first transferred to a sterile stainless steel container. The sample was washed with PBS several times and then the adipose tissue sample was cut with a length of 2 cm and transferred to a tube of 50 ml, and herein, additionally washed and treated with 70% ethanol for anti-infection, and then washed several times with PBS added with an antibiotic mixture (50 IU/ml of penicillin and 50 µg/ml of streptomycin (purchased from Invitrogen)) until the solution was cleaned.

2). Example 2-2: Isolation and Incubation of Mesenchymal Stem Cells from Human Adipose Tissue The isolated adipose tissue was washed with PBS and finely cut, shaken once per 10 min at 37° C. by using a DMEM medium added with collagenase type1 (1 mg/ml), and digested for 1 hr. Next, the adipose tissue was washed with PBS and centrifuged for 5 min at 1000 rpm. A supernatant was suctioned and a pellet remaining on the bottom was washed with PBS and centrifuged for 5 min at 1000 rpm. It was filtered by a filter having a mesh size of 100 µm and washed with PBS after removing debris.

For isolation/incubation of the mesenchymal stem cells, the explanted tissue was immersed in 5 ml of a Dulbecco's modified eagle medium (DMEM) F-12 (Gibco) added with 10% fetal bovine serum (FBS, Hyclone), 10% FBS, 100 unit/ml of penicillin, and 50 µg/ml of streptomycin and maintained at 37° C. in a cell incubator of nitrogen 95% and carbon dioxide 5%, and cells except for the stem cells were killed while maintaining a hypoxic state to increase purity of the mesenchymal stem cells. The medium was replaced every 3 or 4 days. The outgrowth of the cells was monitored by an optical microscope. The outgrown cells were treated with Trypsin (0.125% Trypsin/0.05% EDTA) for additional expansion and refrigeration (using DMEM/10% FBS).

For extraction of the mesenchymal stem cells, pellets of the cells were resuspended and counted in the medium DMEM F-12 (Gibco), 10% FBS, 100 unit/ml of penicillin, and 50 µg/ml of streptomycin and inoculated on a tissue culture dish of 10 cm at a density of $1 \times 10^6$ cells/dish. The medium was replaced every 3 or 4 days. The growth and clone formation of the cells were monitored by an optical microscope. In approximately 90% cell number (confluence), the cells were sub-cultured as described above.

(i) Experimental Example 1: Induction of Pluripotent Stem Cells from Adipose-Derived Mesenchymal Stem Cells Experimental Example 1-1: Manufacture of Pluripotent Stem Cells of Human Adipose-Derived Mesenchymal Stem Cells According to Concentration of Ecklonia cava Extract in Example 1-1

As an experiment for inducing pluripotent stem cells from human adipose-derived stem cells according to a concentration of a Jeju Ecklonia cava extract, in a control group, DMEM F-12 (Gibco) as a dedicated medium of MSC, 10% FBS, 100 unit/ml of penicillin, and 50 µg/ml of streptomycin were used as a basic medium, and in an experimental group, human adipose-derived mesenchymal stem cells which was subjected to three sub-cultures were used, and in the medium, the Jeju Ecklonia cava extract having concentrations of normal, 1 µg/ml, 20 µg/ml, 50 µg/ml, 100 µg/ml, 400 µg/ml, 800µ/ml, and 1 mg/ml and 0.1 v/v % of energy water (purified deionized water containing $SiO_2$, $Al_2O_3$, $TiO_3$, $Fe_2O_3$, CaO, $Na_2O$, $K_2O$, and LiO, STC nara) were added (see FIG. 1). The human adipose-derived mesenchymal stem cells were isolated and washed and monocytes were inoculated in a 6-well plate (dish) with $1 \times 10^4$ cells and maintained and incubated at 37° C. and 5% $CO_2$.

As a result, in the experimental group, it was observed that only when the concentration of the Jeju Ecklonia cava extract was 100 to 400 µg/ml, colonies were formed after 10 days (see FIG. 2), and in this case, the microscope magnification was observed at 200× magnification.

(ii) Experimental Example 1-2: Manufacture of Pluripotent Stem Cells of Human Adipose-Derived Mesenchymal Stem Cells According to Concentration of Ecklonia cava Extract in Example 1-2

Experimental Example 1-2 was experimented by the same method as Experimental Example 1-1 and a Jeju Ecklonia cava extract which was prepared in Example 1-2 was used. As a result, in the experimental group, it was observed that only when the concentration of the Jeju Ecklonia cava extract was 20 to 50 µg/ml, colonies were formed after 10 days (see FIG. 3), and in this case, the microscope magnification was observed at 200× magnification.

(iii) Experimental Example 1-3: Immunochemical Staining Analysis of Pluripotent Stem Cells Induced by Method of the Present Disclosure With respect to the pluripotent stem cells induced by the methods of Experimental Examples 1 and 2, whether to express specific genes OCT4 and SOX2 and protein of stage-specific embryonic antigen-4 (SSEA-4) to the embryonic stem cells was analyzed by using antibodies thereto and whether to express the protein was analyzed by using an immunochemical staining method.

In the staining process, cells were first fixed by using 4% paraformaldehyde and washed with PBS, and blocked with a 1% BSA solution. The cells were treated with primary antibodies for OCT4, SOX3, and SSEA-4 and reacted at 4° C. for 18 hours, and then washed with PBS, treated with secondary antibodies with fluorescence pigment (fluorescein isothiocyanate, FITC) to the primary antibodies, and reacted at room temperature for 1 hour.

The cells were washed with PBS and then the expression was analyzed by using a fluorescence microscope, and the result thereof was illustrated in FIGS. 4 and 5. The BF means a bright field and the second diagram means a staining result for each protein expression, and the third diagram illustrates a cell nucleus strained with DAPI.

As a result, in both the Ecklonia cava extract extracted by using ethanol (Experimental Example 1-1) and the Ecklonia cava extract extracted by using water (Experimental Example 1-2), the pluripotent stem cells having a positive reaction only in the colony of OCT4, SOX2, and SSEA-4 as pluripotent stem cell-specific markers were verified (see FIGS. 4 and 5).

(iv) Experimental Example 1-4: Comparison of Gene Analysis of Pluripotent Stem Cells While the pluripotent stem cells manufactured in Experimental Examples 1-1 and 1-2 was observed by a microscope, only the colony was picked by using a pipette of 200 µl, and then the total RNA was isolated by using a TRIzol reagent (manufactured by Invitrogen Corporation). cDNA was synthesized by using reverse transcription-polymerase chain reaction (RT-PCR) and the PCR was performed by using a specific primer to OCT4, Sox-2, and Nanog genes and glyceraldehyde 3-phosphate dehydrogenase (GAPDH) gene as a control gene. The Nanog, OCT4, and Sox-2 are specific genes in the embryonic stem cells. The PCR products were analyzed by agarose gel electrophoresis and results of verifying expression of these genes were illustrated in FIGS. 6 and 7.

As a result, as illustrated in FIGS. 6 and 7, in mesenchymal stem cells (MSC, control group) without an induction process, an expression level of OCT4, SOX2 and Nanog as specific genes of the pluripotent stem cells is low, whereas in the pluripotent stem cells manufactured by the pluripotent stem cells (Experimental Example 1-1 (illustrated by EtOH EPN) and Experimental Example 1-2 (illustrated by Sonic EPN) induced by the method of the present disclosure, these specific genes were significantly highly expressed. The expression level of OCT4, SOX2 and Nanog as the stem cell genes can be clearly verified through graphs of FIGS. 6 and 7.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for manufacturing stem cells expressing Oct4, SOX2 and Nanog, comprising:
    (a) adding an Ecklonia cava extract which is extracted by water to a cell culture medium in an amount of 20-50 µg/ml relative to a volume of the cell culture medium, or by anhydrous or water-containing low alcohol having 1 to 4 carbon atoms to the cell culture medium in an amount of 10-400 µg/ml relative to the volume of the cell culture medium; and
    (b) culturing mammalian adipose-derived mesenchymal stem cells in the cell culture medium where the Ecklonia cava extract has been added to dedifferentiate into stem cells expressing Oct4, SOX2 and Nanog, wherein the stem cells are capable of differentiating into endoderm, ectoderm and mesodermal cells.

2. The method of claim 1, wherein the cell culture medium is selected from the group consisting of a Dulbecco's modified eagle's medium (DMEM), a minimal essential medium (MEM), a basal medium eagle (BME), RPMI 1640, F-10, F-12, DMEM F-12, a-minimal essential medium (a-MEM), a Glasgow's minimal essential medium (G-MEM), an Iscove's modified Dulbecco's medium (IDMM), and a MacCoy's 5A medium.

3. The method of claim 1, wherein the cell culture medium further comprises 0.01-10% (v/v) of purified deionized water containing $SiO_2$, $Al_2O_3$, $TiO_3$, $Fe_2O_3$, CaO, $Na_2O$, $K_2O$, and LiO.

* * * * *